United States Patent [19]
Lehmann et al.

[11] Patent Number: 6,027,899
[45] Date of Patent: Feb. 22, 2000

[54] METHOD FOR DETERMINING PROPENSITY FOR DEVELOPING LATE-ONSET ALZHEIMER'S DISEASE

[75] Inventors: Donald J. Lehmann, East Sussex; Carole Johnston; Anthony David Smith, both of Oxford, all of United Kingdom

[73] Assignee: Bristol-Myers Squibb Company, Princeton, N.J.

[21] Appl. No.: 09/150,540

[22] Filed: Sep. 9, 1998

Related U.S. Application Data

[60] Provisional application No. 60/058,733, Sep. 12, 1997.

[51] Int. Cl.$^7$ .............................. C12Q 1/68; C12P 19/34; C07H 21/04
[52] U.S. Cl. ........................... 435/6; 435/91.2; 536/23.5; 536/24.31
[58] Field of Search ..................... 435/6, 91.2; 536/23.5, 536/24.31

[56] References Cited

U.S. PATENT DOCUMENTS

| | | | |
|---|---|---|---|
| 5,508,167 | 4/1996 | Roses et al. | 435/6 |
| 5,807,671 | 9/1998 | Soreq et al. | 435/6 |

FOREIGN PATENT DOCUMENTS

WO96/21744  7/1996  WIPO .

OTHER PUBLICATIONS

Mesulam, M.–M. et al, (1992) Cholinesterases in the amyloid angiopathy of Alzheimer's disease, Ann. Neurol. 31, 565–569.

Mesulam, M.–M. et al (1994) Butyrylcholinesterase reactivity differentiates the amyloid plaques of aging from those of dementia, Ann. Neurol. 36, 722–727.

Geula, C. et al, (1995) Cholinesterases and the pathology of Alzheimer disease, Alzheimer Dis. Assoc. Disorders, 9(Suppl. 2), 23–28.

Gomez–Ramos, P. et al (1994) Ultrastructural localization of butyrylcholinesterase on neurofibrillary degeneration sites in the brains of aged and Alzheimer's disease patients, Brain res., 640, 17–24.

Bartels, C.F. et al (1992) DNA mutation associated with the human butyrylcholinesterase K–variant and its linkage to the atypical variant mutation and ot polymorphic sites, Am. J. Hum. Genet. 50, 1086–1103.

Evans, R.T. et al (1984) On the identification and frequency of the J and K cholinesterase phenotypes in a Caucasian population, J. Med. Genet. 21, 99–102.

Whittaker, M. et al (1985) Plasma cholinesterase variants. Family studies of the $E_1^k$ gene, Hum. Hered. 35, 364–368.

Saunders, A.M. et al (1993) Association of apolipoprotein E allele ε4 with late–onset familial and sporadic Alzheimer's disease, Neurology 43, 1467–1472.

Roses, A.D. (1996) Apoliporotein E alleles as risk factors in Alzheimer's disease, Annu. Rev. Med. 47, 387–400.

Van Rensburg, S.J. et al (1993) Increased frequency of the transferrin C2 subtype in Alzheimer's disease, Neuroreport 4, 1269–1271.

Wright, C.I. et al (1993) Neuroglial cholinesterases in the normal brain and in Alzheimer's disease: relationship to plaques, tangles, and patterns of selective vulnerability, Ann. Neurol., 34, 373–384.

Diedrich, J.F. et al (1991) Neuropathological changes in scrapie and Alzheimer's disease are associated with increased expression of apolipoprotein–E and cathepsin–D in astrocytes, J. Virol, 65, 4759–4768.

Roessmann, U. et al (1966) Changes in butyryl cholinesterase activity in reactive glia, Neurology 16, 123–129.

Weisgraber, K.H. et al (1994) Lipoproteins, neurobiology, and Alzheimer's disease: structure and funciton of apolipoprotein E, Curr. Opin. Struct. Biol., 4, 507–515.

Namba, Y. et al (1991) Apolipoprotein E immunoreactivity in cerebral amyloid deposits and neurofibrillary tangles in Alzheimer's disease and kuru plaque amyloid in Creutzfeldt–Jakob disease, Brain Res., 541, 163–166.

Rebeck, G.W. et al (1993) Apolipoprotein–E in sporadic Alzheimer's disease—allelic variation and receptor interactions, Neuron, 11, 575–580.

Nathan, B.P. et al (1994) Differential effects of apolipoproteins E3 and E4 on neuronal growth in vitro, Science 264, 850–852.

Hoffman, A. et al (1997) Atherosclerosis, apolipoprotein E, and prevalence of dementia and Alzheimer's disease in the Rotterdam study, Lancet, 349, 151–154.

Lehmann, D.J. et al, "Synergy between the genes for butyrylcholinesterase K variant and apolipoprotein E4 in late–onset confirmed Alzheimer's disease", Human Molecular Genetics, 1997, vol. 11, 1933–1936.

*Primary Examiner*—Carla J. Myers
*Attorney, Agent, or Firm*—Burton Rodney

[57] ABSTRACT

A method is provided for determining the propensity or predisposition of a human subject to develop late-onset Alzheimer's disease by the presence in a human subject of a gene (1) for butyrylcholinesterase K variant, and a gene (2) for apolipoprotein E4, the presence of the gene (1) or the presence of both of the above genes (1) and (2) indicating a propensity or predisposition to develop late-onset Alzheimer's disease.

11 Claims, No Drawings

METHOD FOR DETERMINING PROPENSITY FOR DEVELOPING LATE-ONSET ALZHEIMER'S DISEASE

This application claims the benefit of U.S. Provisional Application 60/058,733, filed Sep. 12, 1997.

FIELD OF THE INVENTION

The present invention relates to a method for determining the propensity or predisposition of a human subject to develop late-onset Alzheimer's disease through the presence of a gene for butyryl-cholinesterase K variant or the presence of genes for both butyrylcholinesterase K variant and apolipoprotein E4.

BACKGROUND OF THE INVENTION

Alzheimer's disease is a progressive neurodegenerative disorder which causes irreversible damage to brain cells leading to dementia and ultimately death. It is characterized by formation of amyloid plaques and neurofibrillary tangles in the brain. Currently, it is primarily diagnosed by exclusion of other known causes of dementia. Diagnosis at an early stage prior to irreversible changes is practically nonexistent.

In order for therapeutic intervention to be significantly effective in treating Alzheimer's disease, it will have to be administered very early on prior to such irreversible changes. Accordingly, a biological marker which could flag patients who have a propensity or predisposition to developing Alzheimer's disease and thus could be a guide to early diagnosis would be a most-welcomed addition to the diagnostician's armamentarium.

Butyrylcholinesterase (BChE) (located on chromosome 3) is expressed in most human tissues (1), yet its function is unknown. BChE activity in the brain increases with age over 60 years and is elevated in Alzheimer's disease (AD) (2,3). Histochemically reactive BChE is associated with amyloid plaques and neurofibrillary tangles and with amyloid angiopathy in AD (4–8).

A large number of human genetic variants of BChE are known, two of the more common variants being the atypical allele (referred to as the A variant) and the K variant (BCHE-K). The A variant has an Asp70Gly mutation and is rare (0.5% allelic frequency), while the K variant has a point mutation at nucleotide 1615 (GCA→ACA) which changes alanine 539 to threonine and the catalytic activity is reduced by a third (9). BCHE-K is thought to have an allelic frequency of around 12% in Caucasians (9–11).

Until now, there has not been any known connection or association of AD with either the A variant or the K variant.

That the gene for apolipoprotein E4 (APOE ∈4 allele) is a risk factor for AD is well established (12, 13). In fact, the likelihood of a carrier of APOE ∈4 allele developing AD is 7-fold greater than a control who does not carry such gene.

DESCRIPTION OF THE INVENTION

It has now been found that the gene for butyrylcholinesterase K-variant is about twice as common in patients with late-onset AD as compared to controls (without taking into account the presence of the APOE ∈4 gene), while the A variant had little or no connection with AD. Thus, a human subject carrying the gene for BCHE-K has a propensity or predisposition to develop late-onset AD which is about twice that of a human who does not carry such gene.

Furthermore, surprisingly and unexpectedly, it has been found that the presence of both the genes for BCHE-K and for APOE ∈4 is about 30 times as common in patients with late-onset AD as compared to controls. Thus, there is an unexpected synergy between the genes for BCHE-K and APOE ∈4 in late-onset confirmed AD.

In accordance with the invention, a method is provided for determining the propensity or predisposition of a human subject to develop late-onset Alzheimer's disease (AD), which includes the step of detecting the presence or absence of a gene for butyrylcholinesterase K variant in a human subject. The presence of the gene for butyryl-cholinesterase K variant indicates an increased propensity or predisposition of the human subject to develop late-onset Alzheimer's disease as compared to a human control who does not carry the gene.

In fact, it has been found that a human subject carrying the gene for butyrylcholinesterase K variant (BCHE-K) (or a nearby gene on chromosome 3) has at least a 2-fold increase in risk or predisposition to develop late-onset Alzheimer's disease than a human control who does not carry the gene for BCHE-K (without regard to the presence of the apolipoprotein E4 gene).

In addition, in accordance with the present invention, a method is provided for determining the propensity or predisposition of a human subject to develop late-onset Alzheimer's disease, which includes the steps of detecting the presence or absence in a human subject of a gene for butyrylcholinesterase K variant, and detecting the presence or absence in the same human subject of a gene for apolipoprotein E4, the presence of both the genes for butyryl-cholinesterase K variant and apolipoprotein E4 indicating an increased propensity, predisposition or susceptibility to develop late-onset Alzheimer'disease as compared to a human control who carries neither of these 2 genes or only one of the genes.

Surprisingly and unexpectedly it has been found that a synergy exists between the genes for butyrylcholinesterase K variant and apolipoprotein E4 in late-onset confirmed Alzheimer's disease. Thus, a human subject carrying both of the genes will have at least a 30-fold increase in propensity, predisposition or susceptibility to develop late-onset Alzheimer's disease as compared to a human control who does not carry either of the genes.

In addition, a human subject carrying both of the genes will have at least a 7-fold increase in propensity, predisposition of susceptibility to develop late-onset Alzheimer's disease as compared to a human control who carries only the gene for apolipoprotein E4.

The term "late-onset Alzheimer's disease" as employed herein refers to the onset of Alzheimer's disease (the patient displays recognized clinical symptoms indicating Alzheimer's disease) after the age 65.

The terms "apolipoprotein E4" and "APOE ∈4" are used interchangeably to refer to the ∈4 allele of apolipoprotein E.

The terms "butyrylcholinesterase K variant" and "BCHE-K" are used interchangeably to refer to the gene for the K variant of butyrylcholinesterase located at 3q26.1–q26.2 which serves as a predictor or marker for Alzheimer'disease by itself or in conjunction with the gene for apolipoprotein E4. BCHE-K may or may not be implicated in a causal relation to the development of late-onset Alzheimer's disease, and which may, in fact, involve a gene closely located to BCHE-K on chromosome 3, for example, the gene for transferrin at 3q21–q25.

The terms "propensity", "predisposition" or "susceptibility" are used interchangeably with reference to developing Alzheimer's disease.

In carrying out the methods of the invention, a biological source of DNA, such as a blood sample, is taken from human subjects and controls and PCR (polymerase chain reaction) methods used to detect the presence of the genes for (1) butyrylcholinesterase K variant (using the method of Jensen, F. S. et al (1996), Detection of the plasma K variant by PCR using an amplification-created restriction site, Hum. Hered. 46, 26–31), and (2) apolipoprotein E4 (using the method of Wenham, P. R. et al Apolipoprotein E genotyping by one-stage PCR, Lancet 337, 1158–1159).

The biological source of DNA which may be used to detect the presence of the above genes includes any suitable cells readily available through scrapings and the like and those available through biopsy, such as blood cells (including platelets), skin cells, oral mucosal cells, nasal mucosal cells, muscle cells, bone cells, or neurons, with blood cells being preferred.

EXAMPLE

The following clinical tests were carried out to determine if there is synergy between the genes for butyrylcholinesterase K variant and apolipoprotein E4 in late-onset confirmed Alzheimer's disease.

Patients and Methods

282 Caucasians from the Oxford region of England recruited into the Oxford Project to Investigate Memory and Aging (OPTIMA) (38) were examined. 88 were autopsy confirmed CERAD (39) 'definite or probable' AD cases (74 late-, i.e. over 65y, and 14 early-onset), 29 were pathologically confirmed cases of other dementias (12 vascular, 5 Parkinson's, 5 non-specific neurodegeneration, 3 Pick's, 1 each of progressive supranuclear palsy, normal pressure hydrocephalus, Huntington's, glioma), 61 were living cases diagnosed 'possible AD' or 'probable AD' by the National Institutes of Neurology and Communicative Disorders—Alzheimer's disease and Related Disorders Association Work Group (NINCDS/ADRDA) (40) criteria (31 late- and 30 early-onset) and 104 were controls without cognitive impairment with CAMDEX (41) scores>80 (14 had died and had no AD pathology on necropsy). Subjects were genotyped blind to diagnosis, using blood samples, by PCR methods for the atypical and K variants of BCHE (42) and for APOE (43).

Results

After 189 subjects had been genotyped, three control subjects out of 115 and three AD cases out of 74 were identified as heterozygotes for the atypical BCHE allele. Thus, no association was found between histopathologically confirmed AD and the atypical allele of BCHE. Two out of the six atypical BCHE heterozygotes were carriers of BCHE-K.

Altogether 282 Caucasian subjects were genotyped for BCHE-K and for APOE alleles. BCHE-K was more common in late-onset AD cases than in early-onset AD cases, other dementias or controls (Table 1). For subjects aged over 65, the allelic frequency of BCHE-K was 0.09 in 104 controls and 0.17 in 74 confirmed AD cases, giving an odds ratio of AD for BCHE-K of 2.15 (Table 2) (without taking account whether the subjects were carriers of APOE ∈4 gene). Most of this association appeared to be due to subjects over 75y old, for whom the frequency of BCHE-K was 0.08 in 68 controls and 0.19 in 36 confirmed AD cases ($X^2$ with Yates' correction=4.7; p=0.03), giving an odds ratio of AD of 2.7 (Table 2). Although there were insufficient cases for this trend with age to reach significance, the data for the >75y subgroup as well as for all subjects >65y are shown in Tables 2–5.

Taking account of an individual's carrier status for APOE ∈4 produced striking results. In subjects >65y without APOE ∈4 the allelic frequency of BCHE-K was 0.14 in 22 confirmed AD cases and 0.11 in 72 controls. There was thus no association of BCHE-K with late-onset AD in subjects lacking an APOE ∈4 allele. In APOE ∈4 carriers, however, BCHE-K allelic frequencies in subjects aged >65y were 0.18 in 52 confirmed AD cases and only 0.03 in 32 controls; in subject aged >75y the frequencies were 0.23 in 24 confirmed AD cases and 0.02 in 22 controls. These results gave odds ratios of confirmed AD of 6.9 and 12.8 for BCHE-K in APOE ∈4 carriers aged >65y and >75y, respectively (Table 2). For comparison, Table 3 shows the odds ratios of confirmed AD for APOE ∈4 in BCHE-K carriers. It can be seen that an individual's BCHE-K status markedly influences the strength of the effect of APOE ∈4. Table 4 shows the striking differences between cases and controls in the proportions of subjects who carry both BCHE-K AND APOE ∈4 alleles.

All these findings indicated an interaction between BCHE-K and APOE ∈4, which is confirmed by logistic regression analysis. Several logistic regression models were fitted to the data and it was found that a parsimonious model with only APOE ∈4, BCHE-K and their interaction gave an adequate fit (residual deviance: 5.5 on 4 degrees of freedom). In this model, APOE ∈4 and its interaction with BCHE-K were significantly associated with AD, but BCHE-K by itself was not.

In order to examine further the strength of the interaction between BCHE-K and APOE ∈4, Table 5 shows the observed odds ratios of confirmed AD for subjects with different combinations of these two genes, taking subjects who have neither gene as the reference. In subjects over 65y, the odds ratio in those who only carry BCHE-K was 1.1 and in those with only APOE ∈4 it was 3.8. This gave a predicted odds ratio of 4.2 in subjects with both genes, on the assumption of independent effects of the two genes, compared with the observed value of 30.2. In subjects over 75y the predicted odds ratio was 1.7, but the observed odds ratio was 36. Thus, there appears to be a strong synergy between these two alleles in late-onset AD.

It was also found that in 108 subjects (>65y) with dementia all with autopsy diagnosis, 71 subjects with confirmed AD, the presence of APOE ∈4 (without BCHE-K) gave 67% sensitivity and 45% false-positives for AD; the presence of BCHE-K (without APOE ∈4 ) gave 32% sensitivity and 16% false-positives for AD; and the presence of both BCHE-K and APOE ∈4 gave 25% sensitivity and 3% false-positives for AD. The NINCDS criteria gave 94% sensitivity, but 43% false positives, while the NINCDS criteria and both alleles (BCHE-K and APOE ∈4 ) gave 47% sensitivity and 5% false-positives for AD.

Thus, it is seen that adding BCHE-K as a risk factor to APOE ∈4 allele greatly decreases the false-positive rate in diagnosis of AD.

Discussion

That APOE ∈4 is a risk factor for AD is well established (12, 13). The results shown herein are consistent with the hypothesis that BCHE-K is associated with and is a marker or predictor for further increase in the risk of late-onset AD in APOE ∈4 carriers. It is theorized that the effect could be due to linkage disequilibrium with another gene on chromosome 3, conceivably transferrin, whose C2 variant was reported to be more common in 20 clinically diagnosed AD cases than in the general population (14). BCHE is at 3q26.1–q26.2 (15), while the gene for transferrin is at 3q21–q25 (16). On the other hand, the effect on late-onset AD appears to be mediated by BCHE-K itself.

Biolocical Plausibility

There are various potential interactions between BChE and apolipoprotein E (apoE). Both proteins are produced in quantity in the liver and secreted into the circulation (1, 17). Not only apoe, but probably also BChE, interact with lipoproteins (18, 19). Both proteins are found in astrocytes (20, 21) and in other glia, BChE in oligodendrocytes (22) and apoE in microglia (23). Both proteins occur in AD in plaques, intra- and extracellular neurofibrillary tangles and in association with amyloid angiopathy (7, 8, 24, 25). Furthermore, both BChE and apoE have been implicated in certain models of neurite growth (26–31). In the case of apoE, there are differences between E3 and E4 isoforms (29–31) and, in the case of BChE, it has been suggested that the nature of the attached sugar residues may be important (26–28). It should be noted that the K variant of BChE has an additional threonine residue at position 539, but whether this is a potential O-glycosylation site (or, indeed, a phosphorylation site) remains to be shown. Furthermore, a threonine residue has a high propensity for β-sheet formation (32). In lysozyme, conversion of an isoleucine residue to threonine causes amyloidosis (33), as does conversion of an alanine residue to threonine in transthyretin (34).

Implications for Clinical Genetics

Approximately 6% of the Caucasian population carry genes for both BCHE-K and APOE ∈4, assuming respective allelic frequencies of 0.12 (9–11) and 0.15 (17, 35), while 56% of such population carry neither gene. Thus, several millions of the elderly who carry both these genes are at high risk of developing AD, especially when aged over 75y. The ability to identify such at-risk individuals could serve as a means for targeting subjects for early testing for AD before irreversible damage and possibly for early chemotherapeutic intervention.

TABLE 1

Allelic frequencies of BCHE-K and APOE ε4

| | Number of Subjects | F:M ratio | Mean age# | BCHE-K allele frequency | APOE ε4 allele frequency |
|---|---|---|---|---|---|
| control >65y | 104 | 1.26 | 78.1 | 0.09 | 0.16 |
| All LOAD cases | 105 | 1.50 | 80.9 | 0.16* | 0.40** |
| All EOAD cases | 44 | 1.10 | 65.9 | 0.09 | 0.42** |
| Confirmed LOAD | 74 | 1.39 | 81.4 | 0.17* | 0.41** |
| Confirmed EOAD | 14 | 2.50 | 67.8 | 0.07 | 0.54** |
| Confirmed other dementia | 29 | 0.81 | 76.8 | 0.10 | 0.19 |

LOAD and EOAD are respectively late-onset (>65y) and early-onset Alzheimer's disease.
Ages were at death, if status confirmed, but at last clinical assessment for living subjects. Each of the above groups was in exact Hardy Weinberg equilibrium.
*p < 0.03, **p < 0.0001 ($X^2$ with Yates' correction) v. controls.

TABLE 2

Odds ratios of confirmed late-onset Alzheimer's disease for BCHE-K alleles

| Subjects | Controls | Cases | Odds ratio# | 95% C.I. |
|---|---|---|---|---|
| All >65y | 104 | 74 | 2.15 | 1.1–4.25 |
| All >75y | 68 | 36 | 2.7 | 1.1–6.8 |

TABLE 2-continued

Odds ratios of confirmed late-onset Alzheimer's disease for BCHE-K alleles

| Subjects | Controls | Cases | Odds ratio# | 95% C.I. |
|---|---|---|---|---|
| ApoE ε4 carriers >65y | 32 | 52 | 6.9 | 1.65–29 |
| ApoE ε4 carriers >75y | 22 | 24 | 12.8 | 1.9–86 |

*Ages in Tables 2–5 were at onset for late-onset AD cases and for controls at death, if confirmed, but at last clinical assessment if living.
These odds ratios were based on alleles. The equivalent odds ratios for BCHE-K based on carriers were: 2.3, 2.6, 7.9, 15.0.

TABLE 3

Odds ratios of confirmed late-onset Alzheimer's disease for APOE ε4 alleles

| Subjects | Controls | Cases | Odds ratio | 95% C.I. |
|---|---|---|---|---|
| All >65y | 104 | 74 | 3.6 | 2.2–5.9 |
| All >75y | 68 | 36 | 2.8 | 1.4–5.5 |
| BCHE-K carriers >65y | 17 | 23 | 12.3 | 2.6–58 |
| BCHE-K carriers >75y | 11 | 12 | 15.0 | 1.95–115 |

TABLE 4

Proportions of controls and confirmed late-onset AD cases with both BCHE-K and APOE ε4 alleles

| | Proportions with both alleles | | |
|---|---|---|---|
| Subjects | Controls | Cases | p* |
| All >65y | 2/104 (2%) | 18/74 (24%) | <0.0001 |
| All >75y | 1/68 (1%) | 10/36 (28%) | <0.0001 |
| APOE ε4 carriers, >65y | 2/32 (6%) | 18/52 (35%) | 0.007 |
| APOE ε4 carriers, >75y | 1/22 (5%) | 10/24 (42%) | 0.009 |

*$X^2$ with Yates' correction.

TABLE 5

Odds ratios of confirmed late-onset AD, taking subjects who had neither APOE ε4 nor BCHE-K as the reference

| APOE ε4 | BCHE-K | Controls | Cases | Odds ratio | 95% C.I. |
|---|---|---|---|---|---|
| Age >65y | | | | | |
| — | — | 57 | 17 | Reference | |
| — | + | 15 | 5 | 1.1 | NS |
| + | — | 30 | 34 | 3.8 | 1.8–8.1 |
| + | + | 2 | 18 | 30.2 | 8.4–108 |
| Age >75y | | | | | |
| — | — | 36 | 10 | Reference | |
| — | + | 10 | 2 | 0.7 | NS |
| + | — | 21 | 14 | 2.4 | 0.8–7.3 |
| + | + | 1 | 10 | 36.0 | 6.1–211 |

REFERENCES

1. Silver, A. (1974) *The biology of cholinesterases* (North Holland publications, Amsterdam).
2. Perry, E. K., et al (1978) Changes in brain cholinesterases in senile dementia of the Alzheimer type. *Neuropath. Appl. Neurobiol.* 4, 273–277.

3. Perry, E. K. (1980) The cholinergic system in old age and Alzheimer's disease. *Ageing* 9, 1–8.
4. Carson, K. S., et al (1991) Electron microscopic localization of cholinesterase activity in Alzheimer brain tissue. *Brain Res.* 540, 204–208.
5. Mesulam, M. -M., et al (1992) Cholinesterases in the amyloid angiopathy of Alzheimer's disease. *Ann. Neurol.* 31, 565–569.
6. Mesulam, M. -M. and Geula, C. (1994) Butyrylcholinesterase reactivity differentiates the amyloid plaques of aging from those of dementia. *Ann. Neurol.* 36, 722–727.
7. Geula, C. and Mesulam, M. -M. (1995) Cholinesterases and the pathology of Alzheimer disease. *Alzheimer Dis. Assoc. Disorders* 9 (Suppl. 2), 23–28.
8. Gómez-Ramos, P., et al (1994) Ultrastructural localization of butyrylcholinesterase on neurofibrillary degeneration sites in the brains of aged and Alzheimer's disease patients. *Brain res.* 640, 17–24.
9. Bartels, C. F., et al (1992) DNA mutation associated with the human butyrylcholinesterase K-variant and its linkage to the atypical variant mutation and other polymorphic sites. *Am. J. Hum. Genet.* 50, 1086–1103.
10. Evans, R. T. and Wardell, J. (1984) On the identification and frequency of the J and K cholinesterase phenotypes in a Caucasian population. *J. Med. Genet.* 21, 99–102.
11. Whittaker, M. and Britten, J. J. (1985) Plasma cholinesterase variants. Family studies of the $E_1^k$ gene. *Hum. Hered.* 35, 364–368.
12. Saunders, A. M., et al (1993) Association of apolipoprotein E allele ∈c4 with late-onset familial and sporadic Alzheimer's disease. *Neurology* 43, 1467–1472.
13. Roses, A. D. (1996) Apolipoprotein E alleles as risk factors in Alzheimer's disease. *Annu. Rev. Med.* 47, 387–400.
14. Van Rensburg, S. J., et al (1993) Increased frequency of the transferrin C2 subtype in Alzheimer's disease. *Neuroreport* 4, 1269–1271.
15. Gaughan, G., et al (1991) Refinement of the localization of human butyrylcholinesterase to chromosome 3q26.1–q26.2 using a PCR-derived probe. *Genomics* 11, 455–458.
16. Yang, F., et al (1984) Human transferrin: cDNA characterization and chromosomal localization. *Proc. Natl. Acad. Sci. USA* 81, 2752–2756.
17. Mahley, R. W. (1988) Apolipoprotein E: Cholesterol transport protein with expanding role in cell biology. *Science* 240, 622–630.
18. Lawrence, S. H. and Melnick, P. J. (1961) Enzymatic activity related to human serum beta-lipoprotein: histochemical, immunoelectrophoretic and quantitative studies. *Proc. Soc. exp. Biol. Med.* 107, 998–1001.
19. Kutty, K. M., et al (1973) Interrelationship between serum β-lipoprotein and cholinestease. *Can. J. Biochem.* 51, 883–887.
20. Wright, C. I., et al (1993) Neuroglial cholinesterases in the normal brain and in Alzheimer's disease: relationsh to plaques, tangles, and patterns of selective vulnerability. *Ann. Neurol.* 34, 373–384.
21. Diedrich, J. F., et al (1991) Neuropatho-logical changes in scrapie and Alzheimer's disease are associated with increased expression of apolipoprotein-E and cathepsin-D in astrocytes. *J. Virol.* 65, 4759–4768.
22. Roessmann, U. and Friede, R. L. (1966) Changes in butyryl cholinesterase activity in reactive glia. *Neurology* 16, 123–129.
23. Weisgraber, K. H., et al (1994) Lipoproteins, neurobiology, and Alzheimer's disease: structure and function of apolipoprotein E. *Curr. Opin. Struct. Biol.* 4, 507–515.
24. Namba, Y., et al (1991) Apolipoprotein E immunoreactivity in cerebral amyloid deposits and neurofibrillary tangles in Alzheimer's disease and kuru plaque amyloid in Creutzfeldt-Jakob disease. *Brain Res.* 541, 163–166.
25. Rebeck, G. W., et al (1993) Apolipoprotein-E in sporadic Alzheimer's disease—allelic variation and receptor interactions. *Neuron* 11, 575–580.
26. Layer, P. G. and Kaulich, S. (1991) Cranial nerve growth in birds is preceded by cholinesterase expression during neural crest cell migration and the formation of an HNK-1 scaffold. *Cell Tissue Res.* 265, 393–407.
27. Layer, P. G., et al (1993) Cholinesterases regulate neurite growth of chick nerve cells in vitro by means of a non-enzymatic mechanism. *Cell Tissue Res.* 273, 219–226.
28. Layer, P. G. and Willbold, E. (1995) Novel functions of cholinesterases in development, physiology and disease. *Prog. Histochem. Cytochem.* 29(3), 1–94.
29. Nathan, B. P., et al (1994) Differential effects of apolipoproteins E3 and E4 on neuronal growth in vitro. *Science* 264, 850–852.
30. Holtzman, D. M., et al (1995) Low density lipoprotein receptor-related protein mediates apolipoprotein E-dependent neurite outgrowth in a central nervous system-derived neuronal cell line. *Proc. Natl. Acad. Sci. USA* 92, 9480–9484.
31. Nathan, B. P., et al (1995) The inhibitory effect of apolipoprotein E4 on neurite outgrowth is associated with microtubule depolymerization. *J. Biol. Chem.* 270, 19791–19799.
32. Minor, D. L. and Kim, P. S. (1994) Measurement of the beta-sheet-forming propensities of amino acids. *Nature* 367, 660–663.
33. Pepys, M. B., et al (1993) Human lysozyme gene mutations cause hereditary systemic amyloidosis. *Nature* 362, 553–7.
34. Saraiva, M. J., et al (1992) A new transthyretin mutation associated with amyloid cardiomyopathy. *Am. J. Hum. Genet.* 50, 1027–30.
35. Utermann, G., et al (1982) Genetic control of human apolipoprotein E polymorphism: comparison of one- and two-dimentional techniques of isoprotein analysis. *Hum. Genet.* 60, 344–351.
36. Roses, A. D. (1997) A model for susceptibility polymorphisms for complex diseases: apolipoprotein E and Alzheimer disease. Neurogenetics 1, 3–11.
37. Hoffman, A., et al (1997) Atherosclerosis, apolipoprotein E, and prevalence of dementia and Alzheimer's disease in the Rotterdam study. *Lancet* 349, 151–154.
38. Jobst, K. A., et al (1992) Detection in life of confirmed Alzheimer's disease using a simple measurement of medial temporal lobe atrophy by computed tomography. *Lancet* 340, 1179–1183.
39. Mirra, S. S., et al (1991) The Consortium to Establish a Registry for Alzheimer's Disease (CERAD). 2. Standardization of the neuropathologic assessment of Alzheimer's disease. *Neurology* 41, 479–486.
40. McKhann, G., et al (1984) Clinical diagnosis of Alzheimer's disease: report of the NINCDS-ADRDA work group under the auspices of the Department of Health and Human Services task force of Alzheimer's disease. *Neurology* 34, 939–944.
41. Roth, M., et al (1988) CAMDEX: *The Cambridge examination for mental disorders of the elderly* (Cambridge University Press, Cambridge).
42. Jensen, F. S., et al (1996) Detection of the plasma cholinesterase K variant by PCR using an amplification-created restriction site. *Hum. Hered.* 46, 26–31.

43. Wenham, P. R., et al (1991) Apolipoprotein E genotyping by one-stage PCR. *Lancet* 337, 1158–1159.

What is claimed is:

1. A method for determining the propensity or predisposition of a human subject to develop late-onset Alzheimer's disease, which comprises detecting the presence or absence of a gene for butyrylcholinesterase K variant in a human subject, the presence of the gene for butyrylcholinesterase K variant indicating an increased propensity or predisposition of the human subject to develop late-onset Alzheimer's disease as compared to a human subject who does not carry said gene.

2. The method as defined in claim 1 wherein a human subject carrying the gene for butyryl-cholinesterase K variant has a propensity or predisposition to develop late-onset Alzheimer's disease at least about twice that of a human control who does not carry said gene.

3. A method for determining the propensity or predisposition of a human subject to develop late-onset Alzheimer's disease, which comprises detecting the presence or absence in the human subject of a gene for butyrylcholinesterase K variant, and detecting the presence or absence in the human subject of a gene for apolipoprotein E4, the presence of both the genes for butyryl-cholinesterase K variant and apolipoprotein E4 indicating an increased propensity or predisposition to develop late-onset Alzheimer's disease as compared to a human subject who carries neither of said genes or only one of said genes.

4. The method as defined in claim 3 wherein the human subject carrying both the genes for butyrylcholinesterase K variant and apolipoprotein E4 has a propensity or predisposition to develop late-onset Alzheimer's disease at least about 30 times greater than that of a human control who does not carry either of said genes.

5. The method as defined in claim 3 wherein a human subject carrying both the genes for butyrylcholinesterase K variant and apolipoprotein E4 has a propensity or predisposition to develop late-onset Alzheimer's disease at least about 7 times greater than that of a human control, who carries the gene for apolipoprotein E4, but not the gene for butyrylcholinesterase K variant.

6. The method as defined in claim 3 wherein the false-positive rate in diagnoses of Alzheimer's disease where both of said genes are carried by the subject is greatly decreased as compared to false-positive rate where only one of said genes is carried by the subject.

7. The method as defined in claim 6 wherein the false-positive rate in diagnoses of Alzheimer's disease where both of said genes is carried by the subject is about 5% or less.

8. The method as defined in claim 3 including the steps of obtaining a biological sample of DNA from the subject and subjecting the sample to analytical methods to determine the presence or absence of either or both of said genes.

9. The method as defined in claim 8 wherein the biological sample is a sample of blood cells, skin cells, cells of the oral mucosa or nasal passage, muscle cells, bone cells or neurons.

10. The method as defined in claim 9 wherein the cell sample is a sample of blood cells.

11. The method as defined in claim 10 wherein the blood cells are subjected to PCR methods to determine the presence or absence of either or both of said genes.

* * * * *